(12) United States Patent
Osawa (10) Patent No.: US 9,226,681 B2
(45) Date of Patent: Jan. 5, 2016

(54) FIBRILLATION DETECTOR AND DEFIBRILLATOR

(71) Applicant: OLYMPUS CORPORATION, Tokyo (JP)

(72) Inventor: Masato Osawa, Auderghem (BE)

(73) Assignee: OLYMPUS CORPORATION, Tokyo (JP)

( * ) Notice: Subject to any disclaimer, the term of this patent is extended or adjusted under 35 U.S.C. 154(b) by 359 days.

(21) Appl. No.: 13/869,586

(22) Filed: Apr. 24, 2013

(65) Prior Publication Data

US 2014/0121552 A1    May 1, 2014

(30) Foreign Application Priority Data

Oct. 30, 2012 (JP) ................................. 2012-238724

(51) Int. Cl.
| | | |
|---|---|---|
| *A61B 5/0452* | (2006.01) | |
| *A61B 5/046* | (2006.01) | |
| *A61B 5/00* | (2006.01) | |
| *A61B 5/0456* | (2006.01) | |
| *A61N 1/39* | (2006.01) | |

(52) U.S. Cl.
CPC ............... *A61B 5/046* (2013.01); *A61B 5/0456* (2013.01); *A61B 5/7225* (2013.01); *A61B 5/7228* (2013.01); *A61N 1/3925* (2013.01); *A61N 1/3956* (2013.01)

(58) Field of Classification Search
CPC .... A61B 5/0456; A61B 5/046; A61B 5/0452; A61B 5/7228; A61B 5/7225

USPC .................................. 600/509, 515–518, 521
See application file for complete search history.

(56) References Cited

U.S. PATENT DOCUMENTS

| | | | | |
|---|---|---|---|---|
| 5,269,298 A | * | 12/1993 | Adams et al. | ...................... 607/5 |
| 5,891,169 A | | 4/1999 | Boheim et al. | |
| 2012/0123285 A1 | * | 5/2012 | Zhang | ................ A61B 5/04525 |
| | | | | 600/516 |

OTHER PUBLICATIONS

John G. Webster, "Design of Cardiac Pacemakers", IEEE Press, 1995, cited in the Specification (2 pages).

* cited by examiner

*Primary Examiner* — Christopher D Koharski
*Assistant Examiner* — Michael Carey
(74) *Attorney, Agent, or Firm* — Westerman, Hattori, Daniels & Adrian, LLP (57) ABSTRACT

To provide a fibrillation detector and a defibrillator that are capable of correctly detecting within a short time a ventricular fibrillation (VF) that shows an irregular amplitude or shape, an R-wave detection unit R_DETECT_MEAN converts power of a frequency component making up an R wave of an electrocardio signal ECG into an approximately DC component, and outputs the converted power as R-wave power V_R. A T-wave detection unit T_DETECT_MEAN converts power of a frequency component making up a T wave of the electrocardio signal ECG into an approximately DC component, and outputs the converted power as T-wave power V_T. The R-wave power V_R and the T-wave power V_T are input to a comparison unit CMP, and the comparison unit CMP outputs a magnitude comparison result between the R-wave power V_R and the T-wave power V_T as a comparison signal sig_comp.

6 Claims, 9 Drawing Sheets

FIBRILLATION DETECTOR AND DEFIBRILLATOR

BACKGROUND OF THE INVENTION

1. Field of the Invention

The present invention relates to a fibrillation detector that processes an electrocardio signal obtained from a heart of a living body, and a defibrillator including the fibrillation detector.

Priority is claimed on Japanese Patent Application No. 2012-238724, filed Oct. 30, 2012, and published as Japanese Publication No. 2014-087454 (A) on May 15, 2015, the content of which is incorporated herein by reference.

2. Description of Related Art

Figure 9:
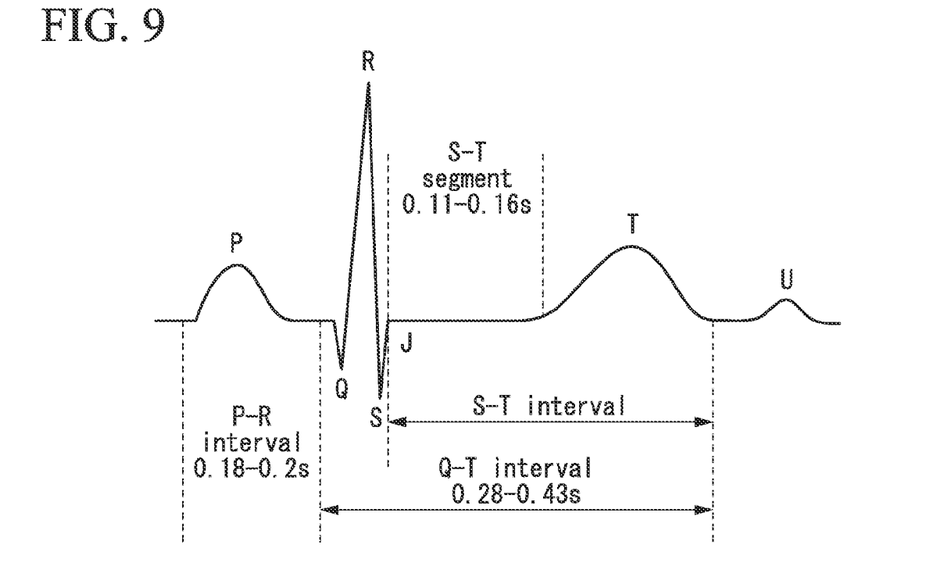
FIG. 9 is a reference diagram illustrating a waveform of an electrocardio signal.

When a heart normally operates, the heart enters a state called a normal sinus rhythm (NSR). Hereinafter, characteristics of the electrocardio gram (ECG) in the NSR state will be described with reference to FIGS. 9 and 10. FIG. 9 shows a diagram cited from FIG. 4.4 of John G. Webster, "Design of Cardiac Pacemakers", IEEE Press (1995), and FIG. 10 shows a diagram cited from FIG. 8.6 of John G Webster, "Design of Cardiac Pacemakers", IEEE Press (1995).

When an ECG in the NSR state is measured, an ECG called QRS waves as shown in FIG. 9 is obtained. FIG. 9 shows a waveform of the ECG In this drawing, a horizontal direction represents time, and a vertical direction represents amplitude. Characteristics of P, Q, R, S, T, and U described in FIG. 9 represent signals called a P wave, a Q wave, an R wave, an S wave, a T wave, and a U wave in the ECG, respectively.

Figure 10:
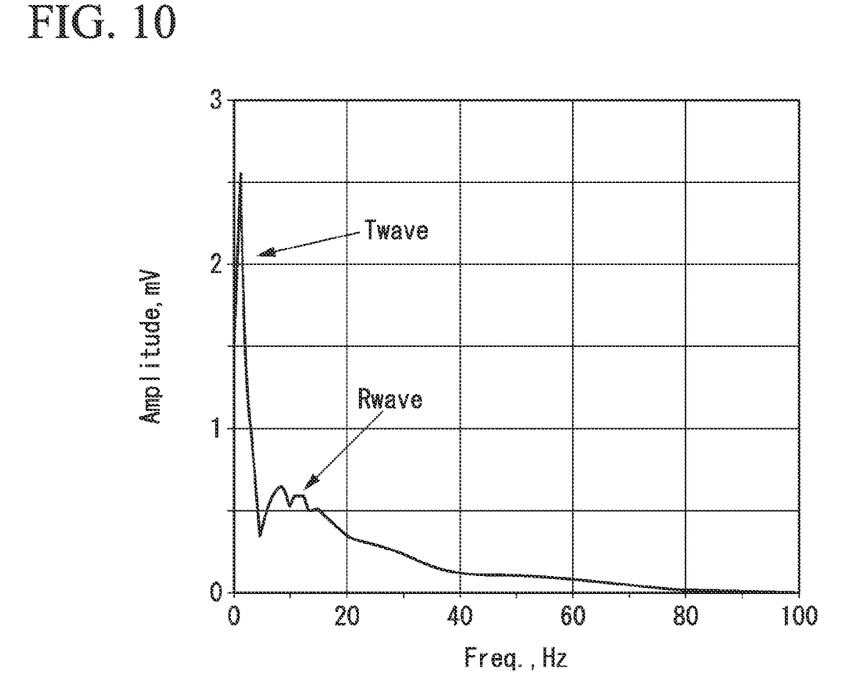
FIG. 10 is a graph illustrating a frequency analysis result of the electrocardio signal.

FIG. 10 shows results obtained by performing a frequency analysis (Fourier transform) of the ECG in the NSR state. From a graph in FIG. 10, it can be seen that the center of a spectrum of the T wave appears at approximately 5 Hz, and the center of a spectrum of the R wave appears at approximately 8 to 15 Hz.

For a patient to which an implantable cardioverter defibrillator (ICD) is applied, a cardiac seizure called a ventricular fibrillation (VF) may occur. When the VF occurs in a patient, the ECG of the patient shows an irregular amplitude or waveform, and as described later, it is difficult to distinguish the QRS waves or T wave. In a case of performing a Fourier transform of the ECG in the VF state, an amplitude of a spectrum, which is present at approximately 8 to 15 Hz and corresponds to the R wave, has a tendency to decrease, and an amplitude of a spectrum, which is near approximately 5 Hz and corresponds to the T wave, has a tendency to increase. The VF causes a circulatory arrest of blood within several seconds, and is the largest cause of sudden cardiac death. Therefore, it is necessary to immediately perform an electrical defibrillation.

Figure 11A:
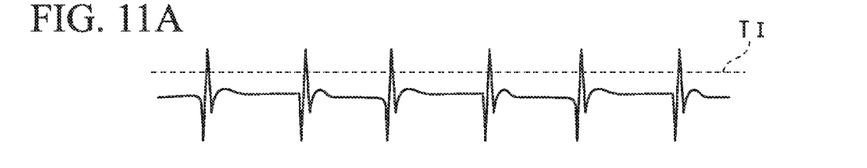
FIG. 11A is a reference diagram illustrating a waveform of the electrocardio signal.
Figure 11B:
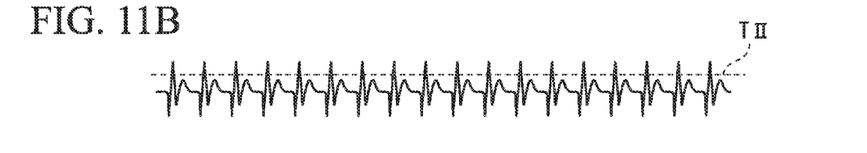
FIG. 11B is a reference diagram illustrating a waveform of the electrocardio signal.
Figure 11C:
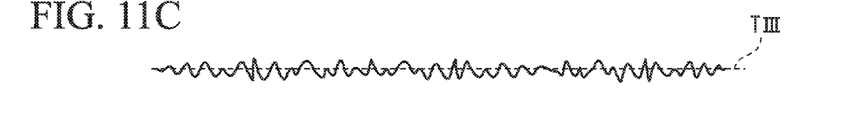
FIG. 11C is a reference diagram illustrating a waveform of the electrocardio signal.
Figure 12A:
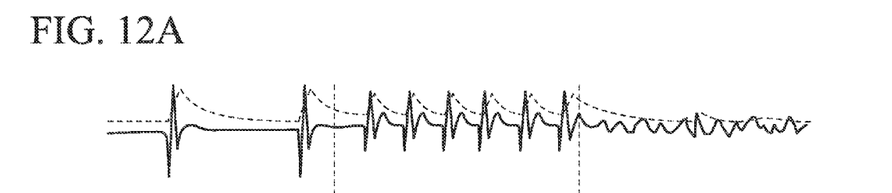
FIG. 12A is a reference diagram illustrating a waveform of the electrocardio signal.
Figure 12B:
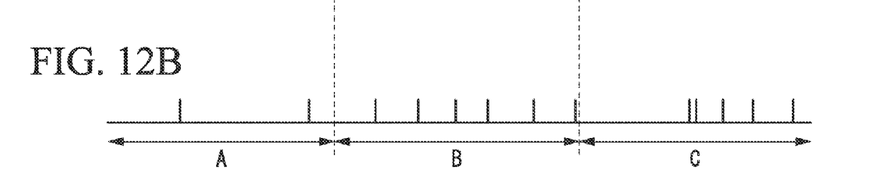
FIG. 12B is a reference diagram illustrating a waveform of the electrocardio signal.

Hereinafter, description will be made with respect to a structure in which the ICD described in the U.S. Pat. No. 5,891,169 detects a cardiac beat with reference to FIGS. 11A, 11B and 11C and 12A and 12B. FIGS. 11A, 11B and 11C show a diagram corresponding to FIG. 2 of the U.S. Pat. No. 5,891,169, and FIGS. 12A and 12B show a diagram corresponding to FIGS. 3A, 3B and 3C of the U.S. Pat. No. 5,891, 169.

FIGS. 11A, 11B and 11C illustrate a method of measuring a cardiac rate using a fixed threshold value. In this drawing, a horizontal direction represents time, and a vertical direction represents amplitude. In this drawing, a solid line represents an ECG, and a broken line represents a threshold value. A portion at which the solid line and the broken line intersect each other is counted as a cardiac beat. The solid line in FIG. 11A represents an ECG of a typical NSR, the solid line in FIG. 11B represents an ECG of a typical ventricular tachycardia (VT), and the solid line in FIG. 11C represents an ECG of a typical VF. In addition, broken lines TI, TII, and TIII represent threshold values that are very suitable to detect cardiac beats of the NSR, VT, and VF, respectively.

In general, when the counted cardiac rate is 145 bpm (beats per minute) or less, it is diagnosed as NSR, when the counted cardiac rate is 146 to 225 bpm, it is diagnosed as VT, and when the counted cardiac rate is 226 bpm or more, it is diagnosed as VF. In addition, when peak values of respective ECGs of the NSR, VT, and VF are compared to each other, the peak value of the VF apparently has a value smaller than those of the NSR and VT. As can be seen from FIGS. 11A, 11B and 11C, when a high threshold value, which is very suitable to detect the cardiac beat of the NSR and VT, is set, the cardiac beat of the VF is not detected, and when a low threshold value, which is very suitable to detect the cardiac beat of the VF, is set, there is a danger that the T wave that is present in the ECG of the NSR and VT is detected as the cardiac beat.

Therefore, as indicated by a broken line in FIG. 12A, a method of detecting the cardiac beat using a threshold value that exponentially attenuates from a peak position of the R wave (the solid line at an upper end of FIGS. 12A and 12B) is generally used. This method is called an AGC method. FIGS. 12A and 12B illustrate a method of measuring the cardiac rate using the AGC method. A solid line in FIG. 12A represents an ECG and a broken line in FIG. 12A represents a threshold voltage in the AGC method. In the drawing, a horizontal direction represents time, and a vertical direction represents amplitude. In a general AGC method, the threshold value has a characteristic of exponentially decreasing from a 75% value of a peak value when detecting the R wave, and a time constant thereof is 400 ms.

A bar graph of FIG. 12B represents a timing at which a cardiac beat is detected, and a portion of a range A in FIG. 12B corresponds to the NSR, a portion of a range B corresponds to the VT, and a portion of a range C corresponds to the VF. As can be seen from this drawing, the cardiac rate in NSR and VT sections is correctly detected.

SUMMARY OF THE INVENTION

According to a first aspect of the invention, there is provided a fibrillation detector including: an R-wave detection unit that converts power of a frequency component making up an R wave of an electrocardio signal obtained from a heart of a living body into an approximately DC component, and outputs the resultant converted DC component as R-wave power; a T-wave detection unit that converts power of a frequency component making up a T wave of the electrocardio signal into an approximately DC component, and outputs the resultant converted DC component as T-wave power; and a comparison unit to which the R-wave power and the T-wave power are input, and which outputs a magnitude comparison result between the R-wave power and the T-wave power as a comparison signal.

In addition, according to a second aspect of the invention, in the fibrillation detector of the invention of the first aspect, a band of the frequency component making up the R wave may be in a range of 10 to 30 Hz, and a band of the frequency component making up the T wave may be in a range of 1 to 12 Hz.

In addition, according to a third aspect of the invention, in the fibrillation detector of the invention of the first aspect, the R-wave detection unit may include a modulation unit that modulates the electrocardio signal by a modulation signal that varies with a frequency larger than the frequency of the R wave by two times, and outputs a modulated signal, an amplification unit to which the modulated signal is input, and which outputs a result obtained by amplifying the modulated signal by predetermined scale factors as a first amplified signal and a second amplified signal, respectively, a first demodulation unit to which the first amplified signal is input, and which outputs, as a first demodulated signal, a result obtained by demodulating the first amplified signal by a first demodulation signal operating with a frequency different from a frequency of the modulation signal within a range of a band of a frequency component making up the R wave, a second demodulation unit to which the second amplified signal is input, and which outputs, as a second demodulated signal, a result obtained by demodulating the second amplified signal by a second demodulation signal having the same frequency as that of the first demodulation signal and having a phase different from a phase of the first demodulation signal by 90°, a first low-pass filter to which the first demodulated signal is input, and which performs low-pass filtering of the first demodulated signal by a first cut-off frequency smaller than a difference between the frequency of the modulation signal and the frequency of the first demodulation signal, and outputs the resultant filtered demodulated signal as a first filtered signal, a second low-pass filter to which the second demodulated signal is input, and which performs low-pass filtering of the second demodulated signal by a second cut-off frequency smaller than a difference between the frequency of the modulation signal and the frequency of the second demodulation signal, and outputs the resultant filtered demodulated signal as a second filtered signal, a power operation unit to which the first filtered signal and the second filtered signal are input, and outputs, as a power signal, a result obtained by performing an operation including a sum of squares operation with respect to the first filtered signal and the second filtered signal, and a third low-pass filter to which the power signal is input, and which outputs, as R-wave power, a power average signal obtained by performing low-pass filtering of the power signal with a frequency smaller than the first cut-off frequency and the second cut-off frequency.

In addition, according to a fourth aspect of the invention, in the fibrillation detector of the invention of the first aspect, the T-wave detection unit may include a modulation unit that modulates the electrocardio signal by a modulation signal that varies with a frequency larger than the frequency of the T wave by two times, and outputs a modulated signal, an amplification unit to which the modulated signal is input, and which outputs a result obtained by amplifying the modulated signal by predetermined scale factors as a first amplified signal and a second amplified signal, respectively, a first demodulation unit to which the first amplified signal is input, and which outputs, as a first demodulated signal, a result obtained by demodulating the first amplified signal by a first demodulation signal operating with a frequency different from a frequency of the modulation signal within a range of a band of a frequency component making up the T wave, a second demodulation unit to which the second amplified signal is input, and which outputs, as a second demodulated signal, a result obtained by demodulating the second amplified signal by a second demodulation signal having the same frequency as that of the first demodulation signal and having a phase different from a phase of the first demodulation signal by 90°, a first low-pass filter to which the first demodulated signal is input, and which performs low-pass filtering of the first demodulated signal by a first cut-off frequency smaller than a difference between the frequency of the modulation signal and the frequency of the first demodulation signal, and outputs the resultant filtered demodulated signal as a first filtered signal, a second low-pass filter to which the second demodulated signal is input, and which performs low-pass filtering of the second demodulated signal by a second cut-off frequency smaller than a difference between the frequency of the modulation signal and the frequency of the second demodulation signal, and outputs the resultant filtered demodulated signal as a second filtered signal, a power operation unit to which the first filtered signal and the second filtered signal are input, and outputs, as a power signal, a result obtained by performing an operation including a sum of squares operation with respect to the first filtered signal and the second filtered signal, and a third low-pass filter to which the power signal is input, and which outputs, as T-wave power, a power average signal obtained by performing low-pass filtering of the power signal with a frequency smaller than the first cut-off frequency and the second cut-off frequency.

In addition, according to a fifth aspect of the invention, in the fibrillation detector of the invention of the third or fourth aspect, the modulation unit, the amplification unit, the first demodulation unit, the second demodulation unit, the first low-pass filter, and the second low-pass filter may be configured as an analog circuit, and the power operation unit and the third low-pass filter may be configured as a digital circuit.

In addition, according to a six aspect of the invention, there is provided a defibrillator including: the fibrillation detector according to the first aspect; a control unit to which the comparison signal is input from the fibrillation detector, and which outputs a defibrillation control signal initiating preparation for defibrillation when it enters a state in which a ventricular fibrillation is informed by the comparison signal, and a defibrillation signal generation unit to which the defibrillation control signal is input, and which applies a defibrillation signal to a heart in a case where fibrillation is not restored within a predetermined time after initiating the preparation of the defibrillation on the basis of the defibrillation control signal.

DETAILED DESCRIPTION OF THE INVENTION

<Defibrillator>

Figure 1:
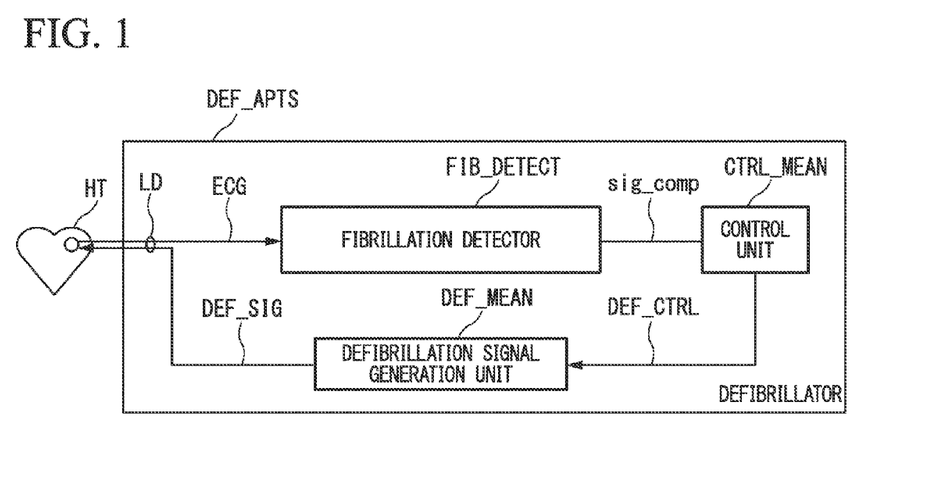
FIG. 1 is a block diagram illustrating a configuration a defibrillator related to an embodiment of the invention.

Hereinafter, an embodiment of the invention will be described with reference to the attached drawings. FIG. 1 shows a configuration of a defibrillator related to an embodiment of the invention. A defibrillator DEF_APTS shown in FIG. 1 includes a fibrillation detector FIB_DETECT, a control unit CTRL_MEAN, and a defibrillation signal generation unit DEF_MEAN.

The fibrillation detector FIB_DETECT is connected to a heart HT and the control unit CTRL_MEAN. An electrocardio signal ECG is input to the fibrillation detector FIB_DETECT from the heart HT via a lead line LD. The fibrillation detector FIB_DETECT determines whether or not the heart HT shows a VF symptom, and outputs a determination result to the control unit CTRL_MEAN as a comparison signal sig_comp. A configuration in which the fibrillation detector FIB_DETECT determines the VF will be described later in detail. The comparison signal sig_comp is a logic signal of a high level ("H") and a low level ("L"). "H" of the comparison signal sig_comp represents that the heart HT shows the VF symptom, and "L" of the comparison signal sig_comp represents that the heart HT enters an NSR or VT state.

The control unit CTRL_MEAN is connected to the fibrillation detector FIB_DETECT and the defibrillation signal generation unit DEF_MEAN. In a case where the comparison signal sig_comp input from the fibrillation detector FIB_DETECT is in the "L", the control unit CTRL_MEAN enters a standby state, and in a case where the comparison signal sig_comp is in the "H", the control unit CTRL_MEAN transmits a defibrillation control signal DEF_CTRL to the defibrillation signal generation unit DEF_MEAN.

The defibrillation signal generation unit DEF_MEAN is connected to the control unit CTRL_MEAN and the heart HT. When receiving the defibrillation control signal DEF_CTRL from the control unit CTRL_MEAN, the defibrillation signal generation unit DEF_MEAN performs preparation for applying a defibrillation signal DEF_SIG to the heart HT, and in a case where the VF does not stop even after a predetermined time has passed and a fibrillation is not recovered, the defibrillation signal generation unit DEF_MEAN applies the defibrillation signal DEF_SIG to the heart HT via the lead line LD.

In addition, in a case where the defibrillation signal DEF_SIG is applied to the heart HT, the VF is stopped due to an electrical shock operation. When a pacing pulse is applied to the heart HT according to necessity, the heart HT returns to an NSR state.

<Fibrillation Detector>

Hereinafter, a configuration and an operation of the fibrillation detector FIB_DETECT related to this embodiment will be described with reference to FIGS. 2 and 3.

<Configuration of Fibrillation Detector FIB_DETECT>

First, a configuration of the fibrillation detector FIB_DETECT will be described with reference to FIG. 2. FIG. 2 shows a configuration of the fibrillation detector FIB_DETECT related to this embodiment. The fibrillation detector FIB_DETECT shown in FIG. 2 includes an R-wave detection unit R_DETECT_MEAN, a T-wave detection unit T_DETECT_MEAN, and a comparison unit CMP.

The R-wave detection unit R_DETECT_MEAN is connected to the heart HT and the comparison unit CMP. The R-wave detection unit R_DETECT_MEAN converts power of a frequency component corresponding to the R wave of the electrocardio signal ECG that is input from the heart HT into approximately DC component, and outputs the resultant converted DC component to the comparison unit CMP as R-wave power V_R.

The T-wave detection unit T_DETECT_MEAN is connected to the heart HT and the comparison unit CMP. The T-wave detection unit T_DETECT_MEAN converts power of a frequency component corresponding to the T wave of the electrocardio signal ECG that is input from the heart HT into approximately DC component, and outputs the resultant converted DC component to the comparison unit CMP as T-wave power V_T.

The comparison unit CMP is connected to the R-wave detection unit R_DETECT_MEAN, the T-wave detection unit T_DETECT_MEAN, and the control unit CTRL_MEAN shown in FIG. 1. The comparison unit CMP outputs a comparison result of a magnitude relationship between the R-wave power V_R and the T-wave power V_T to the control unit CTRL_MEAN as a comparison signal sig_comp.

<Operation of Fibrillation Detector FIB_DETECT>

Next, an operational principle of the fibrillation detector FIB_DETECT will be described in detail with reference to FIGS. 3A, 3B and 3C. FIGS. 3A, 3B and 3C show a temporal variation of a signal at main nodes of the fibrillation detector FIB_DETECT. FIGS. 3A, 3B and 3C correspond to signals to be described later, respectively, and the original point and the scale in regard to the horizontal axis are common in FIGS. 3A, 3B and 3C.

First, an operation of the heart HT will be described with reference to FIG. 3A. The heart HT generates the electrocardio signal ECG and outputs it to the R-wave detection unit R_DETECT_MEAN and the T-wave detection unit T_DETECT_MEAN. The temporal variation of the electrocardio signal ECG is as indicated by a solid line of FIG. 3A. The horizontal axis of a graph described in FIG. 3A represents a time axis and the vertical axis thereof represents a voltage axis. The electrocardio signal ECG enters an NSR state until a time t1, and the electrocardio signal ECG enters a VF state after the time t1. In the NSR section, regular QRS waves as described by using FIG. 11A is continuously present, and in the VF section, an irregular signal as described by using FIG. 11C is continuously present.

Next, an operation of the R-wave detection unit R_DETECT_MEAN and the T-wave detection unit T_DETECT_MEAN will be described with reference to FIG. 3B. The horizontal axis of FIG. 3B represents a time axis and the vertical axis thereof is an axis representing power (square of a voltage). A solid line of FIG. 3B represents a waveform of the R-wave power V_R that is output from the R-wave detection unit R_DETECT_MEAN. A broken line of FIG. 3B represents a waveform of a signal obtained by multiplying the T-wave power V_T output from the T-wave detection unit T_DETECT_MEAN by a coefficient α. The coefficient α represents a predetermined coefficient (constant) to be described later.

First, the R-wave detection unit R_DETECT_MEAN will be described. The R-wave detection unit R_DETECT_MEAN converts power of a frequency component corresponding to the R wave of the electrocardio signal ECG that is input from the heart HT into an approximately DC component, and outputs the resultant converted DC component to the comparison unit CMP as the R-wave power V_R. As described above, in an NSR section, the R-wave power indicated by the solid line is higher than the T-wave power indicated by the broken line in correspondence with occurrence of the R wave, but since clear R wave does not appear in a VF section, the R-wave power decreases to a level lower than that of the T-wave power indicated by the broken line. In addition, an extraction range of a frequency corresponding to the R wave is configured by frequencies between the minimum frequency and the maximum frequency that set the extraction range, and may be arbitrarily set within a range of 10 to 30 Hz. Since the extraction range of the frequency corresponding to the R wave, which is very suitable for accurately detecting the VF, is different for each patient, an optimal value is set by a doctor during implantation of the defibrillator DEF_APTS.

Next, the T-wave detection unit T_DETECT_MEAN will be described. The T-wave detection unit T_DETECT_MEAN converts power of a frequency component corresponding to the T wave of the electrocardio signal ECG that is input from the heart HT into an approximately DC component, and outputs the resultant converted DC component to the comparison unit CMP as the T-wave power V_T. When the VF occurs, since the frequency component of the R wave that occurs in the NSR state is shifted to a band of the frequency component of the T wave, a level of the T-wave power indicated by the solid line is raised in the VF state. In addition, an extraction range of a frequency corresponding to the T wave is configured by frequencies between the minimum frequency and the maximum frequency that set the extraction range, and may be arbitrarily set within a range of 1 to 12 Hz. Since the extraction range of the frequency corresponding to the T wave, which is very suitable for accurately detecting the VF, is different for each patient, an optimal value is set by a doctor during implantation of the defibrillator DEF_APTS.

Next, an operation of the comparison unit CMP will be described with reference to FIG. 3C. The horizontal axis of FIG. 3C represents a time axis and the vertical axis thereof is an axis representing a logic level. The comparison unit CMP outputs a comparison result of a magnitude relationship between the R-wave power V_R and the T-wave power V_T to the control unit CTRL_MEAN as a comparison signal sig_comp.

The comparison signal sig_comp is set to "L" in a case where the condition of the following Equation (1) is satisfied, and is set to "H" in a case where the condition of the following Equation (2) is satisfied. However, α is a predetermined coefficient, and may be arbitrarily set within a range of 0.001 to 1,000.

$$V\_R > \alpha \times T\_R \tag{1}$$

$$V\_R \leq \alpha \times T\_R \tag{2}$$

Figure 3A:
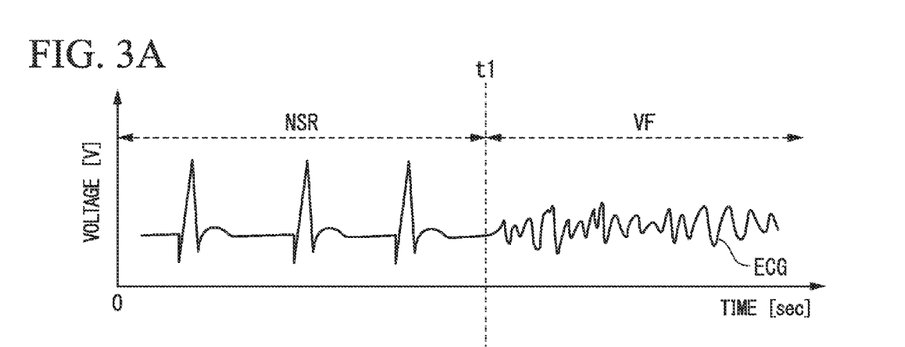
FIG. 3A is a graph illustrating temporal variation of a signal at main nodes of the fibrillation detector related to the embodiment of the invention.
Figure 3B:
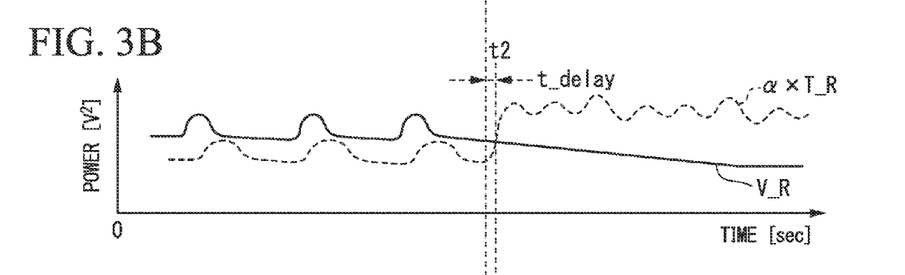
FIG. 3B is a graph illustrating temporal variation of a signal at main nodes of the fibrillation detector related to the embodiment of the invention.
Figure 3C:
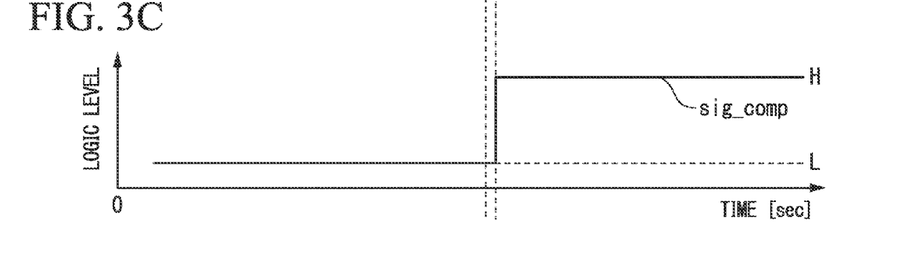
FIG. 3C is a graph illustrating temporal variation of a signal at main nodes of the fibrillation detector related to the embodiment of the invention.

A temporal variation of the comparison signal sig_comp is as described by a solid line of FIG. 3C. The comparison signal sig_comp maintains the "L" state in the NSR section, and transitions to the "H" state after t_delay [sec] has passed from transition into the VF section. As shown in the drawing, the delay time t_delay, which is a difference between a time t1 at which the VF actually begins to start and a time t2 at which the comparison unit CMP begins to output the "H" level, is very small. Commonly, a specific value of the delay time t_delay is a half or less than a time that is necessary for the heart HT to beat once in the NSR state.

As described above, according to the fibrillation detector FIB_DETECT of this embodiment, since a medical phenomenon, in which the R-wave power having a sufficient magnitude in the NSR state becomes very small in the VF state, is detected by a variation in a power spectrum ratio of the R wave and the T wave, even when an absolute value of the electrocardio signal ECG varies steeply, and a VF waveform showing an irregular amplitude or waveform occurs, the VF diagnosis may be accurately carried out within a short time.

In addition, according to the defibrillator DEF_APTS on which the fibrillation detector FIB_DETECT of this embodiment is mounted, preparation of defibrillation therapy may be performed quickly on the basis of a result of accurate and quick diagnosis, and thus the therapy of the VF may be initiated at an earlier time compared to the defibrillator in the related art. Therefore, occurrence of a blood circulatory arrest due to the VF is suppressed, and thus VF therapy having a relatively superior therapeutic effect may be realized.

Details of a simulation result that verifies effectiveness of the fibrillation detector FIB_DETECT of this embodiment will be described later.

Various modifications may be made with respect to the above-described example within a range not departing from the gist of the invention. For example, in the above description, the comparison unit CMP multiplies the T-wave power V_T by the predetermined coefficient α and compares the resultant T-wave power V_T and the R-wave power V_R. However, the coefficient α may be realized by a ratio between an amplification factor while the R-wave detection unit R_DETECT_MEAN amplifies the R-wave power V_R and an amplification factor while the T-wave detection unit T_DETECT_MEAN amplifies the T-wave power V_T. In this case, the comparison unit CMP only performs the magnitude comparison between the R-wave power V_R and the T-wave power V_T.

<R-Wave (T-Wave) Detection Unit>

Hereinafter, a configuration and an operation of the R-wave detection unit R_DETECT_MEAN and the T-wave detection unit T_DETECT_MEAN related to this embodiment will be described in detail with reference to FIGS. 4 and 5A, 5B, 5C, 5D and 5E.

<Configuration of R-Wave Detection Unit R_DETECT_MEAN>

Figure 4:
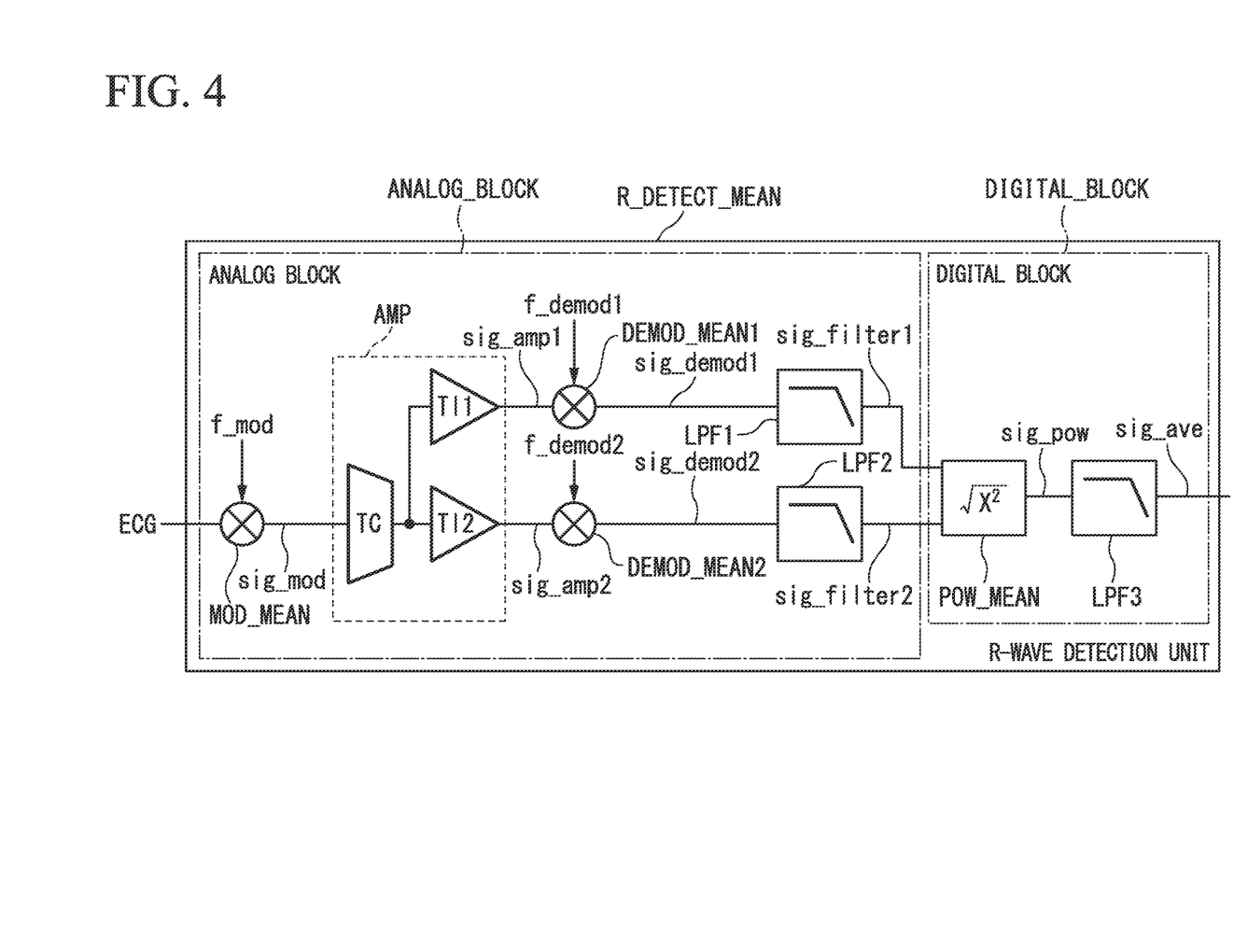
FIG. 4 is a block diagram illustrating a configuration of an R-wave detection unit related to the embodiment of the invention.

First, a configuration of the R-wave detection unit R_DETECT_MEAN will be described with reference to FIG. 4. FIG. 4 illustrates the configuration of the R-wave detection unit R_DETECT_MEAN related to this embodiment. The R-wave detection unit R_DETECT_MEAN includes an analog block ANALOG_BLOCK made up by an analog circuit, and a digital block DIGITAL_BLOCK made up by a digital circuit. The digital block DIGITAL_BLOCK may be realized by a gate array such as a DSP and FPGA, or may be mounted as software on a microcontroller.

First, the analog block ANALOG_BLOCK will be described. The analog block ANALOG_BLOCK includes a modulation unit MOD_MEAN, an amplification unit AMP, a first demodulation unit DEMOD_MEAN1, a second demodulation unit DEMOD_MEAN2, a first low-pass filter LPF1, and a second low-pass filter LPF2.

In addition, the amplification unit AMP includes a transconductance unit TC, a first transimpedance unit TI1, and a second transimpedance unit TI2. The modulation unit MOD_MEAN is connected to the heart HT and the transconductance unit TC making up the amplification unit AMP. A modulation signal f_mod is input to the modulation unit MOD_MEAN from a modulation signal generation unit (not shown). The modulation unit MOD_MEAN modulates the electrocardio signal ECG input from the heart HT to a frequency f1 using the modulation signal f_mod and outputs the resultant modulated signal as a modulated signal sig_mod.

The transconductance unit TC is connected to the modulation unit MOD_MEAN, the first transimpedance unit TI1, and the second transimpedance unit TI2. The transconductance unit TC converts the modulated signal sig_mod, which is input from the modulation unit MOD_MEAN, from a voltage signal to a current signal using a predetermined transconductance value gm, and outputs the resultant converted signal to the first transimpedance unit TI1 and the second transimpedance unit TI2.

The first transimpedance unit TI1 is connected to the transconductance unit TC and the first demodulation unit DEMOD_MEAN1. The first transimpedance unit TI1 converts the current signal, which is input from the transconductance unit TC, from a current signal to a voltage signal using a predetermined transimpedance value Z, and output the resultant converted signal to the first demodulation unit DEMOD_MEAN1 as a first amplified signal sig_amp1.

The second transimpedance unit TI2 is connected to the transconductance unit TC and the second demodulation unit DEMOD_MEAN2. The second transimpedance unit TI2 converts the current signal, which is input from the transconductance unit TC, from a current signal to a voltage signal using a predetermined transimpedance value Z, and outputs the resultant converted signal to the second demodulation unit DEMOD_MEAN2 as a second amplified signal sig_amp2.

In addition, the product of the transconductance value gm and the transimpedance value Z determines an amplification factor of the first amplified signal sig_amp1 with respect to the modulated signal sig_mod, and an amplification factor of the second amplified signal sig_amp2 with respect to the modulated signal sig_mod. The product of the transconductance value gm and the transimpedance value Z, that is, an amplification factor Av of the amplification unit AMP may be set to a desired value within a range of 1 to 10,000.

The first demodulation unit DEMOD_MEAN1 is connected to the first transimpedance unit TI1 and the first low-pass filter LPF1. A first demodulation signal f_demod1 is input to the first demodulation unit DEMOD_MEAN1 from a modulation signal generation unit (not shown). The first demodulation unit DEMOD_MEAN1 demodulates the first amplified signal sig_amp1 input from the first transimpedance unit TI1 into an approximately DC component using a first demodulation signal f_demod1, and outputs the resultant demodulated signal to the first low-pass filter LPF1 as a first demodulated signal sig_demod1.

The first low-pass filter LPF1 is connected to the first demodulation unit DEMOD_MEAN1 and a power operation unit POW_MEAN. The first low-pass filter LPF1 performs low-pass filtering of the first demodulated signal sig_demod1 input from the first demodulation unit DEMOD_MEAN1 by a first cut-off frequency fc1, and outputs a resultant first filtered signal sig_filter1 to the power operation unit POW_MEAN.

The second demodulation unit DEMOD_MEAN2 is connected to the second transimpedance unit TI2 and the second low-pass filter LPF2. A second demodulation signal f_demod2 is input to the second demodulation unit DEMOD_MEAN2 from a demodulation signal generation unit (not shown). The second demodulation unit DEMOD_MEAN2 demodulates the second amplified signal sig_amp2 input from the second transimpedance unit TI2 into an approximately DC component by the second demodulation signal f_demod2, and outputs the resultant demodulated signal to the second low-pass filter LPF2 as a second demodulated signal sig_demod2.

The second low-pass filter LPF2 is connected to the second demodulation unit DEMOD_MEAN2 and the power operation unit POW_MEAN. The second low-pass filter LPF2 performs low-pass filtering of the second demodulated signal sig_demod2 input from the second demodulation unit DEMOD_MEAN2 by a second cut-off frequency fc2, and outputs a resultant second filtered signal sig_filter2 to the power operation unit POW_MEAN.

Next, the digital block DIGITAL_BLOCK will be described. The digital block DIGITAL_BLOCK includes the power operation unit POW_MEAN and a third low-pass filter LPF3.

The power operation unit POW_MEAN is connected to the first low-pass filter LPF1, the second low-pass filter LPF2, and the third low-pass filter LPF3. The power operation unit POW_MEAN performs an A/D conversion of the first filtered signal sig_filter1 input from the first low-pass filter LPF1 and the second filtered signal sig_filter2 input from the second low-pass filter LPF2, and outputs a result obtained by performing an operation including a sum of squares operation with respect to these two signals to the third low-pass filter LPF3 as a power signal sig_pow.

Figure 2:
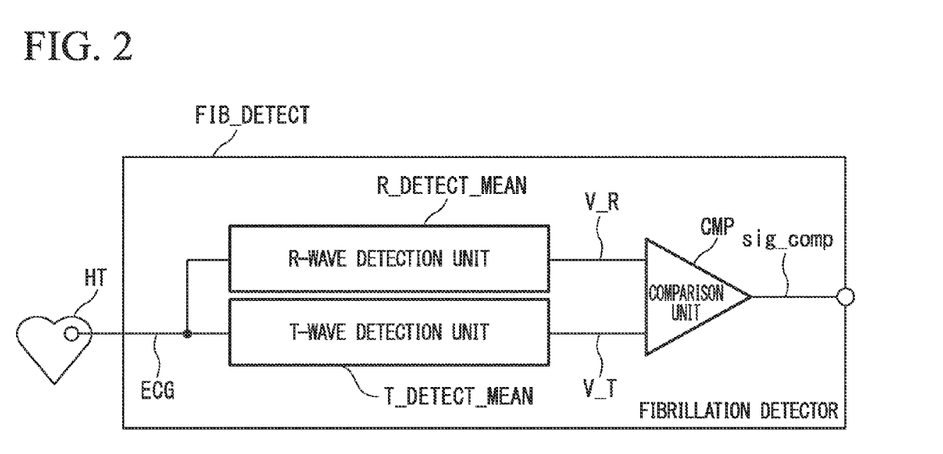
FIG. 2 is a block diagram illustrating a configuration of a fibrillation detector related the embodiment of the invention.

The third low-pass filter LPF3 is connected to the power operation unit POW_MEAN and the comparison unit CMP of FIG. 2. The third low-pass filter LPF3 outputs a power average signal sig_ave, which is a result obtained by smoothing the power signal sig_pow input from the power operation unit POW_MEAN, to the comparison unit CMP. In addition, a power average signal sig_ave that is output from the R-wave detection unit R_DETECT_MEAN is described as the R-wave power V_R in FIG. 2, but these signals are the same signals.

<Configuration of T-Wave Detection Unit T_DETECT_MEAN>

A configuration of the T-wave detection unit T_DETECT_MEAN is the same as the configuration of the R-wave detection unit R-DETECT-MEAN, and thus detailed description thereof will not be repeated. The T-wave detection unit T_DETECT_MEAN is different from the R-wave detection unit R_DETECT_MEAN in the frequencies of the first demodulation signal f_demod1 and the second demodulation signal f_demod2. These different points will be described later in detail. In addition, the power average signal sig_ave that is output from the T-wave detection unit T_DETECT_MEAN corresponds to the T-wave power V_Tin FIG. 2.

<Operation Principle of R-Wave Detection Unit R_DETECT_MEAN>

Hereinafter, an operation principle of the R-wave detection unit R_DETECT_MEAN related to this embodiment will be described in detail with reference to FIGS. 5A, 5B, 5C, 5D and 5E. FIGS. 5A, 5B, 5C, 5D and 5E illustrates a frequency component of a signal at main nodes of the R-wave detection unit R_DETECT_MEAN. FIGS. 5A, 5B, 5C, 5D and 5E correspond to signals to be described, respectively. The horizontal axis represents a frequency, and the vertical axis represents a spectrum amplitude.

Figure 5A:
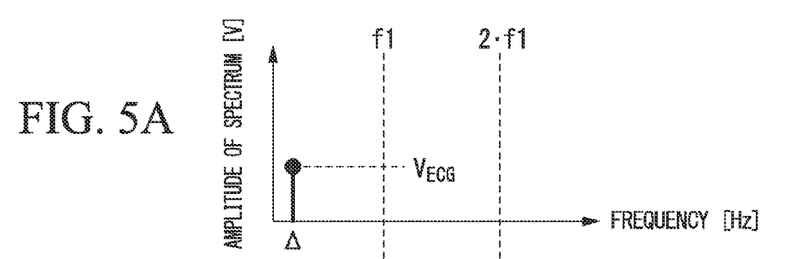
FIG. 5A is a graph illustrating a frequency component of a signal at main nodes of the R-wave detection unit related to the embodiment of the invention.

First, the electrocardio signal ECG will be described with reference to FIG. 5A. In this description, for simplicity, a frequency component (for example, the R wave), which is an object to be detected, of the electrocardio signal ECG is set as a sinusoidal wave having a frequency Δ[Hz], an amplitude $V_{ECG}$[V], and a phase α[°]. This sinusoidal wave is expressed as $V_{ECG}·\sin(2\pi\Delta+\alpha)$. A peak of a spectrum that corresponds to this sinusoidal wave is described in FIG. 5A.

Figure 5B:
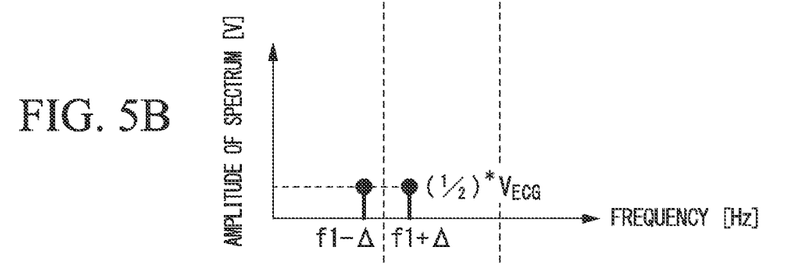
FIG. 5B is a graph illustrating a frequency component of a signal at main nodes of the R-wave detection unit related to the embodiment of the invention.

Next, the demodulated signal sig_mod will be described with reference to FIG. 5B. The demodulated signal sig_mod is generated by the modulation unit MOD_MEAN and is expressed by the product of the electrocardio signal ECG and the modulation signal f_mod having a frequency f1. In addition, it is necessary for the frequency of the demodulation signal f_mod to be larger than a frequency of the R wave by two times so as to establish the following description. This frequency of the R wave is a frequency (for example, a central frequency of a spectrum making up the R wave) within an extraction range of a frequency corresponding to the R wave. As described above, since the extraction range of the frequency corresponding to the R wave, which is very suitable for accurately detecting the VF, is different for each patient, an optimal extraction range is set by a doctor during implantation of the defibrillator DEF_APTS, and a frequency of the modulation signal f_mod is set in accordance with the extraction range.

In a case where the modulation signal f_mod is set to $\sin(2\pi·f1)$, the amplitude $V_{sig\_mod}$ of the demodulated signal sig_mod is as expressed by the following Equation (3). In addition, a frequency characteristic is as shown in FIG. 5B, and peaks appear at frequencies f1−Δ and f1+Δ.

$$V_{sig\_mod} = V_{ECG}\sin(2\pi \cdot \Delta + \alpha) \cdot \sin(2\pi \cdot f1) \quad (3)$$
$$= -(V_{ECG}/2) \cdot \{\cos(2\pi \cdot (f1 + \Delta) + \alpha) - \cos(2\pi \cdot (f1 - \Delta) - \alpha)\}$$

In the following description, the sinusoidal wave is used for modulation and demodulation operations, but even when the modulation signal f_mod is a rectangular wave, the same operation and effect as the argument in the sinusoidal wave may be obtained. This is because the same argument as Equation (3) is established with respect to a frequency component of a tertiary or higher harmonic wave that is a constituent component when the rectangular wave is subjected to Fourier development.

Next, the first amplified signal sig_amp1 and the second amplified signal sig_amp2 will be described with reference to FIG. 5C. The following Equation (4) illustrates an amplitude Vsig_amp1 of the first amplified signal sig_amp1 that is amplified with a predetermined amplification factor Av by the amplification unit AMP, and the following Equation (4') illustrates an amplitude Vsig_amp2 of the second amplified signal sig_amp2 that is amplified with a predetermined amplification factor Av by the amplification unit AMP.

$$V_{sig\_amp1}=(A_V·V_{ECG}/2)·\{-\cos(2\pi·(f1+\alpha)+\alpha)+\cos(2\pi·(f1-\Delta)-\alpha)\} \quad (4)$$

$$V_{sig\_amp2}=(A_V·V_{ECG}/2)·\{-\cos(2\pi·(f1+\alpha)+\alpha)+\cos(2\pi·(f1-\Delta)-\alpha)\} \quad (4')$$

Figure 5C:
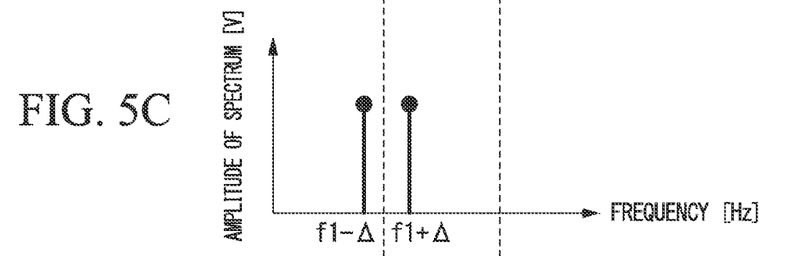
FIG. 5C is a graph illustrating a frequency component of a signal at main nodes of the R-wave detection unit related to the embodiment of the invention.

A frequency characteristic of the first amplified signal sig_amp1 is as shown in FIG. 5C. A frequency characteristic of the second amplified signal sig_amp2 is also the same as the frequency characteristic of the first amplified signal sig_amp1, and is as shown in FIG. 5C.

Next, the first demodulated signal sig_demod1 will be described with reference to FIG. 5D. The first demodulated signal sig_demod1 is generated by the first demodulation unit DEMOD_MEAN1 and is expressed by the product of the first amplified signal sig_amp1 and the first demodulation signal f_demod1.

Figure 5D:
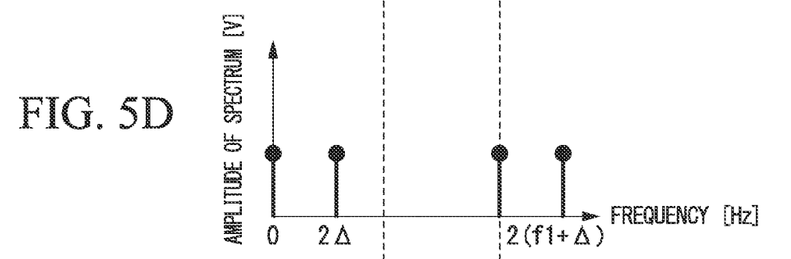
FIG. 5D is a graph illustrating a frequency component of a signal at main nodes of the R-wave detection unit related to the embodiment of the invention.

In a case where the first demodulation signal f_demod1 is a sinusoidal wave having a frequency of f1+Δ[Hz] and a phase 0[°], that is, $\sin(2\pi·(f1+\Delta))$, the amplitude $V_{sig\_demod1}$ of the first demodulation signal f_demod1 is as expressed by Equation (5), and a frequency characteristic thereof is as shown in FIG. 5D.

$$V_{sig\_demod1} = V_{sig\_amp1} \cdot \sin(2\pi \cdot (f1 + \Delta)) \quad (5)$$
$$= (A_V \cdot V_{ECG}/2) \cdot$$
$$[(-1/2)\{\sin(2\pi \cdot (2f1 + 2\Delta) + \alpha) + \sin(\alpha)\} +$$
$$(1/2)\{\sin(2\pi \cdot (2f1) - \alpha) + \sin(2\pi \cdot (2\Delta) - \alpha)\}]$$

In addition, Δ is set to a frequency (for example, a central frequency of a spectrum making up the R wave) of the R wave, and may be arbitrarily set within a range of 10 to 30 Hz. As described above, since the extraction range of the frequency corresponding to the R wave, which is very suitable for accurately detecting the VF, is different for each patient, an optimal extraction range is set by a doctor during implantation of the defibrillator DEF_APTS, and the value of α is set in accordance with the extraction range.

As can be seen from Equation (5), in the demodulation operation of this embodiment, in addition to the DC component, harmonic waves that have frequencies of 2×f1, 2×(f1+Δ), and 2×Δ, respectively, are generated. However, since these harmonic waves are not used for VF diagnosis, these harmonic waves are filtered (removed) by a low-pass filter to be described later. The calculation of a case in which the frequency of the first demodulation signal f_demod1 is f1−Δ[Hz] is omitted, but ultimately the same effect as the case in which the frequency of the first demodulation signal f_demod1 is f1+Δ[Hz] may be obtained.

Next, the first filtered signal sig_filter1 will be described with reference to FIG. 5E. The first filtered signal sig_filter1 is a signal obtained by low-pass filtering of the first demodulated signal sig_demod1 by the first cut-off frequency fc1. The first cut-off frequency fc1 may be set to an arbitrary value smaller than Δ, and is preferably set within a range in which the R wave of the electrocardio signal ECG, which is different depending on a patient, has a sufficient amplitude. For example, in an electrocardio signal ECG of any patient, in a case where the frequency component corresponding to the R wave has a peak at 12±2 Hz, Δ of 12 Hz and fc1 of 2 Hz are preferable setting values. When setting is performed in this manner, only a frequency component, which is within a range of 10 to 14 Hz, of the electrocardio signal ECG is included in the first filtered signal sig_filter1, and unnecessary signals such as the T-wave component having a frequency of approximately 5 Hz and an external ham signal of 50 Hz are suppressed.

Terms other than sin(α) shown in Equation (5) are removed by the first low-pass filter LPF1, and thus a voltage $V_{sig\_filter1}$ of the first filtered signal sig_filter1 is given as the following Equation (6).

$$V_{sig\_filter1} = (A_V \cdot V_{ECG}/4) \cdot \sin(\alpha) \quad (6)$$

Figure 5E:
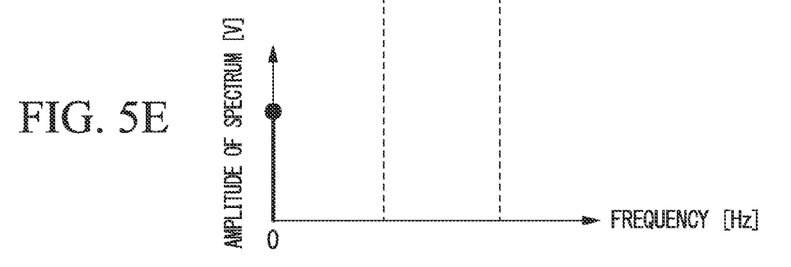
FIG. 5E is a graph illustrating a frequency component of a signal at main nodes of the R-wave detection unit related to the embodiment of the invention.

In addition, a frequency characteristic of the first filtered signal sig_filter1 is as shown in FIG. 5E, and a peak appears at a DC component.

Next, the second demodulated signal sig_demod2 will be described with reference to FIG. 5D. The second demodulated signal sig_demod2 is generated by the second demodulation unit DEMOD_MEAN2, and is expressed by the product of the second amplified signal sig_amp2 and the second demodulation signal f_demod2.

In addition, since the second demodulation signal f_demod2 is a sinusoidal wave having a frequency of f1±Δ[Hz] and a phase of 90[°], and is equivalent to a cosine wave having a phase of 0[°]. In a case where the second demodulation signal f_demod2 is set to cos(2π·(f1+Δ)), the amplitude Vsig_demod2 of the second demodulation signal f_demod2 is as expressed by the following Equation (7). A frequency characteristic is as shown in FIG. 9D.

$$V_{sig\_demod2} = V_{sig\_amp2} \cdot \cos(2\pi \cdot (f1 + \Delta)) \quad (7)$$
$$= (A_V \cdot V_{ECG}/2) \cdot$$
$$[(-1/2)\{\cos(2\pi \cdot (2f1 + 2\Delta) + \alpha) + \cos(\alpha)\} +$$
$$(1/2)\{\cos(2\pi \cdot (2f1) - \alpha) + \cos(2\pi \cdot (2\Delta) - \alpha)\}]$$

In Equation (7), in addition to the DC component, harmonic waves that have frequencies of 2×f1, 2×(f1+Δ), and 2×Δ, respectively, are generated. However, since these harmonic waves are not used for VF diagnosis, these harmonic waves are filtered by a low-pass filter to be described later. The calculation of a case in which the frequency of the second demodulation signal f_demod2 is f1−Δ[Hz] is omitted, but ultimately the same effect as the case in which the frequency of the first demodulation signal f_demod1 is f1+Δ[Hz] may be obtained.

Next, the second filtered signal sig_filter2 will be described with reference to FIG. 5E. The second filtered signal sig_filter2 is a signal obtained by performing a low-pass filtering of the second demodulated signal sig_demod2 by the second cut-off frequency fc2. The second cut-off frequency fc2 may be set to an arbitrary value smaller than Δ, and is preferably set within a range in which the R wave of the electrocardio signal ECG, which is different depending on a patient, has a sufficient amplitude. For example, in an electrocardio signal ECG of any patient, in a case where the frequency component corresponding to the R wave has a peak at 12±2 Hz, Δ of 12 Hz and fc1 of 2 Hz are preferable setting values. When setting is performed in this manner, only a frequency component, which is within a range of 10 to 14 Hz, of the electrocardio signal ECG is included in the second filtered signal sig_filter2, and unnecessary signals such as the T-wave component having a frequency of approximately 5 Hz and an external ham signal of 50 Hz are suppressed.

Terms other than cos(α) shown in Equation (7) are removed by the second low-pass filter LPF2, and thus a voltage $V_{sig\_filter2}$ of the second filtered signal sig_filter2 is given as the following Equation (8).

$$V_{sig\_filter2} = (A_V \cdot V_{ECG}/4) \cdot \cos(\alpha) \quad (8)$$

In addition, a frequency characteristic of the second filtered signal sig_filter2 is as shown in FIG. 5E, and a peak appears at a DC component.

Hereinafter, the power signal sig_pow will be described. The power signal sig_pow is a result obtained by performing an operation including a sum of squares of the first filtered signal sig_filter1 and the second filtered signal sig_filter2 in the power operation unit POW_MEAN, and a voltage $V_{sig\_pow}$ representing the operation result of the sum of squares is expressed by the following Equation (9).

$$V_{sig\_pow} = (V_{sig\_filter1})^2 + (V_{sig\_filter2})^2 \quad (9)$$
$$= (A_V \cdot V_{ECG}/4)^2 \cdot \{\sin(\alpha)^2 + \cos(\alpha)^2\}$$
$$= (A_V \cdot V_{ECG}/4)^2$$

From this equation, it can be seen that the electrocardio signal ECG having a frequency Δ is converted into the DC signal. This result is true of a case in which the frequency of the first demodulation signal f_demod1 and the second demodulation signal f_demod2 is f1−Δ.

Hereinafter, the power average signal sig_ave will be described. In a case where the electrocardio signal ECG enters an NSR state, an instantaneously large R wave component is generated in a peak of the R-wave. Therefore, it is preferable to average the power signal sig_pow so as to perform a magnitude relationship comparison with the T wave. A cardiac beat occurs approximately every second. Therefore, the power signal sig_pow is subjected to low-pass filtering by a low-pass filter having a time constant that is sufficiently larger than 1 Hz, thereby obtaining the power average signal sig_ave. In this embodiment, the third low-pass filter LPF3 carries out this function. A cut-off frequency fc3 of the third low-pass filter LPF3 is a frequency smaller than the first cut-off frequency fc1 and the second cut-off frequency fc2, and is 0.1 Hz.

<Operation Principle of T-Wave Detection Unit T_DETECT_MEAN>

An operation principle of the T-wave detection unit T_DETECT_MEAN is the same as that of the R-wave detection unit R_DETECT_MEAN, and thus detailed description thereof will not be repeated. Both of these units are different only in a frequency difference Δ of the modulation signal and the demodulation signal and values of the first cut-off frequency fc1 and the second cut-off frequency fc2. As described above, since the frequency component of the typical T wave has a peak within a range of 5±1 Hz, in the T-wave detection unit T_DETECT_MEAN, the value of Δ is preferably 5 Hz, and the values of fc1 and fc2 are preferably 1 Hz.

When fc1 and fc2 are set in this manner, only frequency components, which are within a range of 4 to 6 Hz, of the electrocardio signal ECG are extracted as the first filtered signal sig_filter1 and the second filtered signal sig_filter2. That is, unnecessary signals such as the R-wave component having a frequency of approximately 12 Hz and an external ham signal of 50 Hz are suppressed.

Therefore, only a frequency component, which is within a range of 4 to 6 Hz, of the electrocardio signal ECG is included in the power average signal sig_ave output from the T-wave detection unit T_DETECT_MEAN. This value represents only a typical example, and a frequency range of the component, which is included in the power average signal sig_ave output from the T-wave detection unit T_DETECT_MEAN, of the electrocardio signal ECG may be set to an arbitrary range within a range of 1 to 12 Hz.

As described above, according to the defibrillator FIB_DETECT in which the R-wave detection unit R_DETECT_MEAN and the T-wave detection unit T_DETECT_MEAN of this embodiment are mounted, since a variation in a ratio of the frequency component of the R wave and the frequency component of the T wave is detected by comparison of the power of the R wave and the power of the T wave that are converted into the approximately DC component, even in a state in which the electrocardio signal ECG decreases steeply, the VF diagnosis may be carried out in an accurate and quick manner.

In addition, like this embodiment, when a majority of signal processing, which is performed with respect to the electrocardio signal ECG in which the maximum value of a frequency component is approximately 100 Hz, is performed by an analog circuit, there is a merit of a low-power consuming operation expected in an analog circuit that operates at a low frequency. In a case where the above-described extraction of the frequency component is carried out with an FFT operation algorithm by a digital circuit such as a microcontroller, n×log(n) times of operations are necessary (n: the number of samples of data). The frequency making up the electrocardio signal ECG is a low frequency wave and large n is necessary. Therefore, operation processing may not be performed at a sufficient execution speed with a low power-consumption type microcontroller mounted in implantation medical instrument such as the defibrillator. In addition, in a case where the extraction of the frequency component making up the R wave and the frequency component making up the T wave is carried out by a digital circuit, a large memory is necessary to maintain a sampling result of the low frequency signal.

In this embodiment, since the extraction of the frequency component making up the R wave and the frequency component making up the T wave may be carried out by an analog circuit that may carry out the extraction in real time, it is possible to reduce an amount of signal processing and a memory capacity that are necessary for the digital circuit such as the microcontroller. Therefore, accurate VF diagnosis may be realized with low power-consumption and within a short time compared to the related art.

In addition, it is necessary for the power operation unit POW_MEAN to carry out a square operation, there is a merit in a signal processing by a digital circuit that is capable of securing a sufficient dynamic range. This is because square of 1 mV becomes 1 $\mu V^2$ and square of 2 V becomes 4 $V^2$, and thus a sufficient dynamic range may not be secured in the analogy circuit.

<Test Result>

To confirm the above-described effect, the above-described operation was mounted in a program code of Matlab and a simulation test was carried out. FIGS. 6A, 6B, 6C and 6D shows this result. Instead of the ECG signal from a patient, a VF section is extracted from a ECG waveform data set of AnnAber (http://www.electrogram.com/about.html), and simulation was carried out by the Matlab by connecting four different VF waveforms and SR waveforms.

Figure 6A:
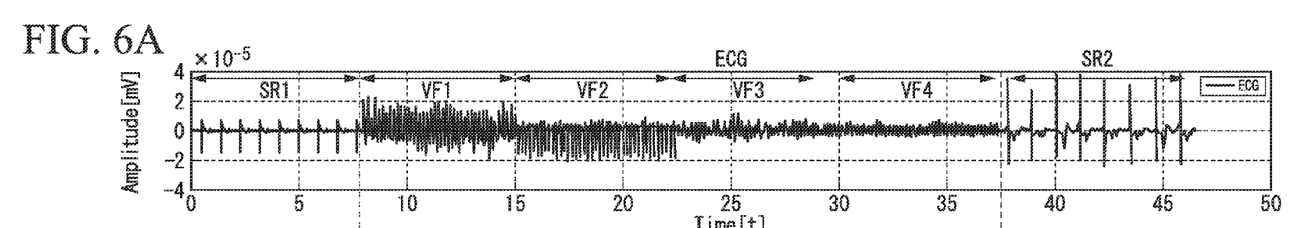
FIG. 6A is a graph illustrating results of a simulation test related to the embodiment of the invention.
Figure 6B:
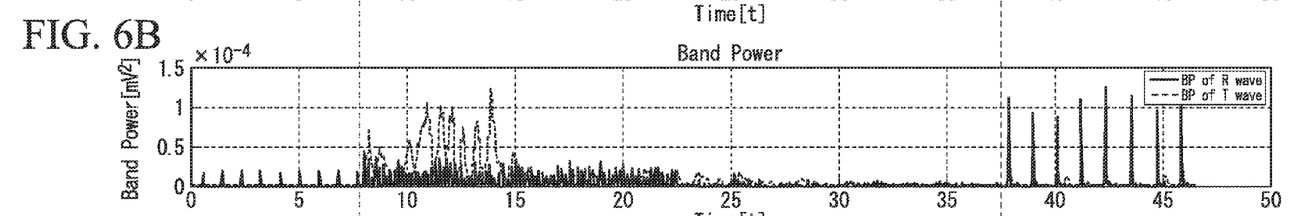
FIG. 6B is a graph illustrating results of a simulation test related to the embodiment of the invention.

FIG. 6A shows an input signal corresponding to the electrocardio signal ECG In FIG. 6A, SR1 and SR2 represent electrocardio signals ECG of different patients in an NSR state, respectively, and VF1, VF2, VF3, and VF4 represent electrocardio signals ECG of different patients in a VF state, respectively. FIG. 6B represents band power of the electrocardio signals ECG described in FIG. 6A. Two lines in the drawing correspond to the power signal sig_pow in the R-wave detection unit R_DETECT_MEAN and the power signal sig_pow in the T-wave detection unit T_DETECT_MEAN, respectively.

Figure 6C:
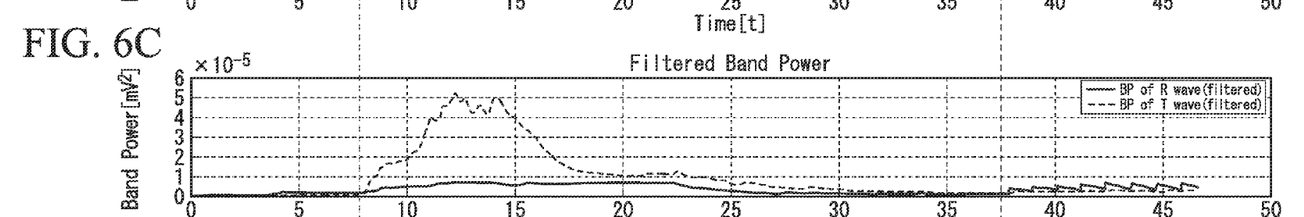
FIG. 6C is a graph illustrating results of a simulation test related to the embodiment of the invention.

FIG. 6C shows an average value of the band power of the electrocardio signals ECG described in FIG. 6A. Two lines in the drawing correspond to the power average signal sig_ave in the R-wave detection unit R_DETECT_MEAN and the power average signal sig_ave in the T-wave detection unit T_DETECT_MEAN, respectively.

Figure 6D:
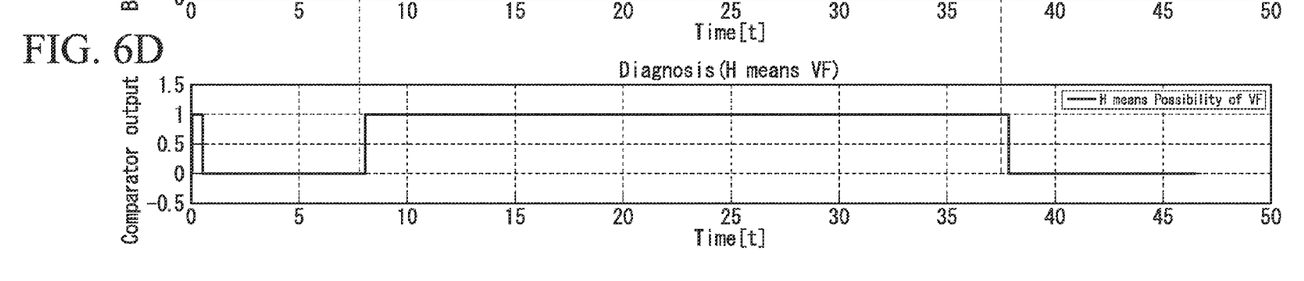
FIG. 6D is a graph illustrating results of a simulation test related to the embodiment of the invention.

FIG. 6D shows a result obtained by comparing the power average signal sig_ave output from the R-wave detection unit R_DETECT_MEAN and the power average signal sig_ave output from the T-wave detection unit T_DETECT_MEAN by the comparison unit CMP. A line in the drawing corresponds to a comparison signal sig_cmp output from the comparison unit CMP. As can be seen from FIG. 6C, since the T-wave power V_T exceeds the R-wave power V_R only in the VF section, the comparison unit CMP immediately outputs the comparison signal sig_cmp of an H level indicating VF in the VF section.

As described above, when the electrocardio signal ECG transitions from the NSR state to the VF state, the comparison unit CMP rapidly follows the transition and outputs the comparison signal sig_cmp of the H level. When the electrocardio signal ECG transitions from the VF state to the NSR state, the comparison unit CMP rapidly follows the transition and outputs the comparison signal sig_cmp of an L level. Therefore, according to the defibrillator FIB_DETECT in which the R-wave detection unit R_DETECT_MEAN and the T-wave detection unit T_DETECT_MEAN of this embodiment are mounted, accurate VF diagnosis may be realized within a short time.

MODIFICATIONS

Figure 7:
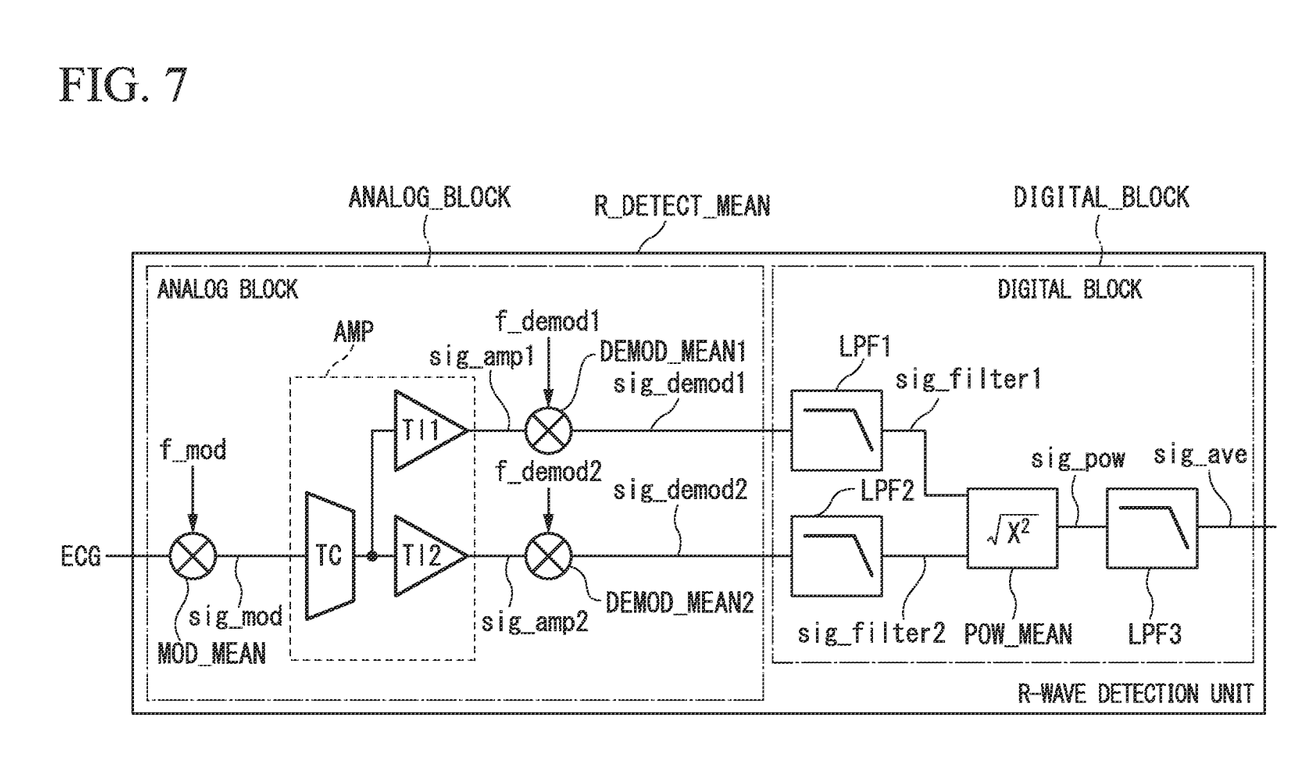
FIG. 7 is a block diagram illustrating another configuration of the R-wave detection unit related to the embodiment of the invention.

Hereinbefore, the embodiment of the invention was described in detail with reference to the attached drawings, but a specific configuration is not limited to the above-described embodiment and includes design change and the like within a range not departing from the gist of the invention. For example, as shown in FIG. 7, the first low-pass filter LPF1 and the second low-pass filter LPF2 that make up the R-wave detection unit R_DETECT_MEAN may belong to the digital block DIGITAL_BLOCK.

Figure 8:
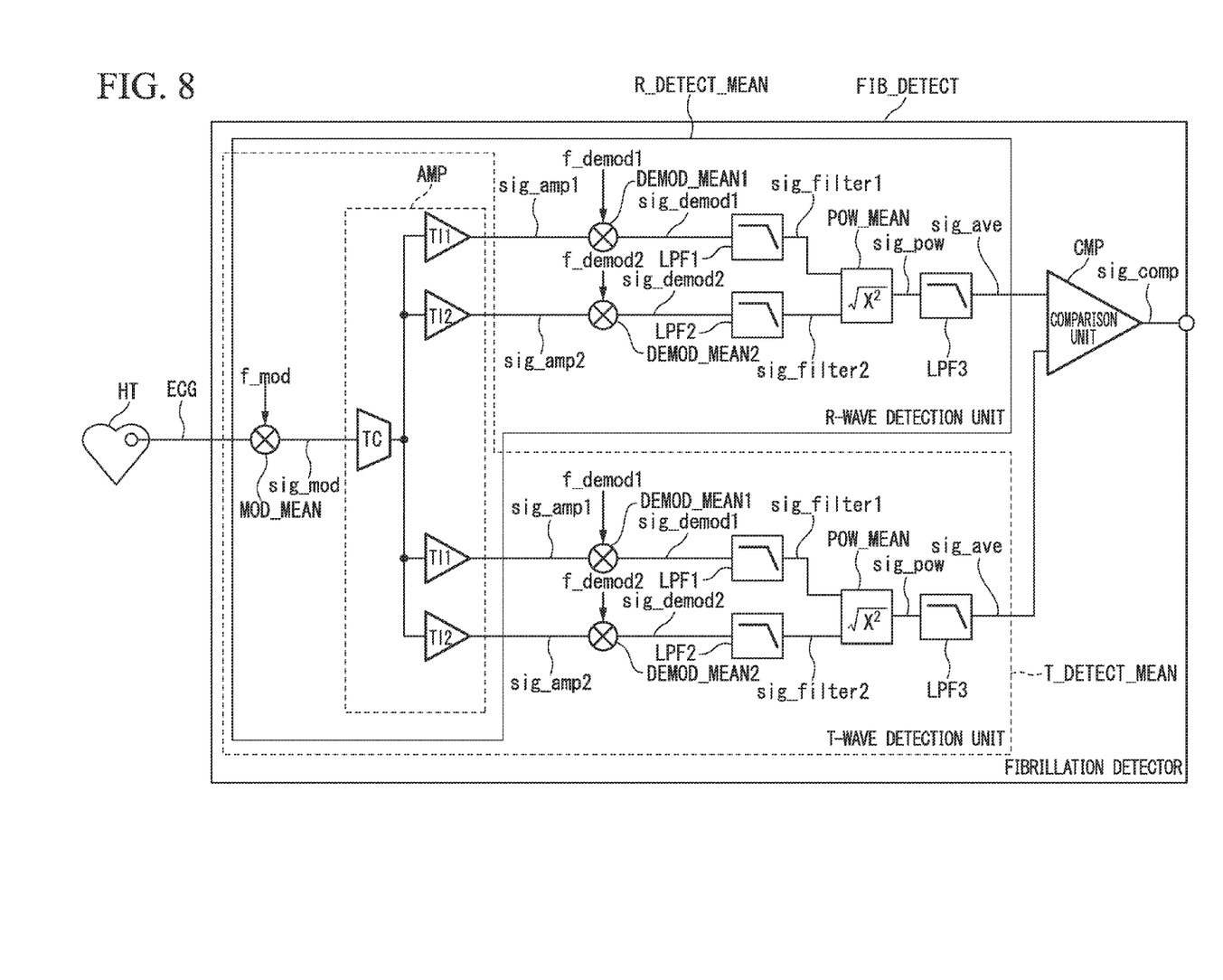
FIG. 8 is a block diagram illustrating another configuration of the fibrillation detector related to the embodiment of the invention.

In addition, as shown in FIG. 8, the modulation unit MOD_MEAN and the amplification unit AMP_MEAN that make up the R-wave detection unit R_DETECT_MEAN may be shared with the modulation unit MOD_MEAN and the amplification unit AMP_MEAN that make up the T-wave detection unit T_DETECT_MEAN.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A fibrillation detector, comprising:
   an R-wave detection unit that converts power of a frequency component making up an R wave of an electrocardio signal obtained from a heart of a living body into an approximately DC component, and outputs the resultant converted DC component as R-wave power;

a T-wave detection unit that converts power of a frequency component making up a T wave of the electrocardio signal into an approximately DC component, and outputs the resultant converted DC component as T-wave power; and a comparison unit to which the R-wave power and the T-wave power are input, and which outputs a magnitude comparison result between the R-wave power and the T-wave power as a comparison signal.

2. The fibrillation detector according to claim 1, wherein a band of the frequency component making up the R wave is in a range of 10 Hz to 30 Hz, and a band of the frequency component making up the T wave is in a range of 1 Hz to 12 Hz.

3. The fibrillation detector according to claim 1, wherein the R-wave detection unit includes, a modulation unit that modulates the electrocardio signal by a modulation signal that varies with a frequency larger than the frequency of the R wave by two times, and outputs a modulated signal, an amplification unit to which the modulated signal is input, and which outputs a result obtained by amplifying the modulated signal by predetermined scale factors as a first amplified signal and a second amplified signal, respectively, a first demodulation unit to which the first amplified signal is input, and which outputs, as a first demodulated signal, a result obtained by demodulating the first amplified signal by a first demodulation signal operating with a frequency different from a frequency of the modulation signal within a range of a band of a frequency component making up the R wave, a second demodulation unit to which the second amplified signal is input, and which outputs, as a second demodulated signal, a result obtained by demodulating the second amplified signal by a second demodulation signal having the same frequency as that of the first demodulation signal and having a phase different from a phase of the first demodulation signal by 90°, a first low-pass filter to which the first demodulated signal is input, and which performs low-pass filtering of the first demodulated signal by a first cut-off frequency smaller than a difference between the frequency of the modulation signal and the frequency of the first demodulation signal, and outputs the resultant filtered demodulated signal as a first filtered signal, a second low-pass filter to which the second demodulated signal is input, and which performs low-pass filtering of the second demodulated signal by a second cut-off frequency smaller than a difference between the frequency of the modulation signal and the frequency of the second demodulation signal, and outputs the resultant filtered demodulated signal as a second filtered signal, a power operation unit to which the first filtered signal and the second filtered signal are input, and outputs, as a power signal, a result obtained by performing an operation including a sum of squares operation with respect to the first filtered signal and the second filtered signal, and a third low-pass filter to which the power signal is input, and which outputs, as R-wave power, a power average signal obtained by performing low-pass filtering of the power signal with a frequency smaller than the first cut-off frequency and the second cut-off frequency.

4. The fibrillation detector according to claim 1, wherein the T-wave detection unit includes, a modulation unit that modulates the electrocardio signal by a modulation signal that varies with a frequency larger than the frequency of the T wave by two times, and outputs a modulated signal, an amplification unit to which the modulated signal is input, and which outputs a result obtained by amplifying the modulated signal by predetermined scale factors as a first amplified signal and a second amplified signal, respectively, a first demodulation unit to which the first amplified signal is input, and which outputs, as a first demodulated signal, a result obtained by demodulating the first amplified signal by a first demodulation signal operating with a frequency different from a frequency of the modulation signal within a range of a band of a frequency component making up the T wave, a second demodulation unit to which the second amplified signal is input, and which outputs, as a second demodulated signal, a result of demodulating the second amplified signal by a second demodulation signal having the same frequency as that of the first demodulation signal and having a phase different from a phase of the first demodulation signal by 90°, a first low-pass filter to which the first demodulated signal is input, and which performs low-pass filtering of the first demodulated signal by a first cut-off frequency smaller than a difference between the frequency of the modulation signal and the frequency of the first demodulation signal, and outputs the resultant filtered demodulated signal as a first filtered signal, a second low-pass filter to which the second demodulated signal is input, and which performs low-pass filtering of the second demodulated signal by a second cut-off frequency smaller than a difference between the frequency of the modulation signal and the frequency of the second demodulation signal, and outputs the resultant filtered demodulated signal as a second filtered signal, a power operation unit to which the first filtered signal and the second filtered signal are input, and outputs, as a power signal, a result obtained by performing an operation including a sum of squares operation with respect to the first filtered signal and the second filtered signal, and a third low-pass filter to which the power signal is input, and which outputs, as T-wave power, a power average signal obtained by performing low-pass filtering of the power signal with a frequency smaller than the first cut-off frequency and the second cut-off frequency.

5. The fibrillation detector according to claim 3, wherein the modulation unit, the amplification unit, the first demodulation unit, the second demodulation unit, the first low-pass filter, and the second low-pass filter are configured as an analog circuit, and the power operation unit and the third low-pass filter are configured as a digital circuit.

6. A defibrillator comprising:

the fibrillation detector according to claim 1;

a control unit to which the comparison signal is input from the fibrillation detector, and which outputs a defibrillation control signal initiating preparation for defibrillation when it enters a state in which a ventricular fibrillation is informed by the comparison signal; and a defibrillation signal generation unit to which the defibrillation control signal is input, and which applies a defibrillation signal to a heart in a case where fibrillation is not restored within a predetermined time after initiating the preparation of the defibrillation on the basis of the defibrillation control signal.

* * * * *